(12) United States Patent
Sternberger et al.

(10) Patent No.: US 9,888,869 B2
(45) Date of Patent: Feb. 13, 2018

(54) NEURAL BLOCK DETERMINATION

(71) Applicant: The Johns Hopkins University, Baltimore, MD (US)

(72) Inventors: Wayne I. Sternberger, Highland, MD (US); Robert S. Greenberg, Glenelg, MD (US)

(73) Assignee: The Johns Hopkins University, Baltimore, MA (US)

( * ) Notice: Subject to any disclaimer, the term of this patent is extended or adjusted under 35 U.S.C. 154(b) by 24 days.

(21) Appl. No.: 14/945,710

(22) Filed: Nov. 19, 2015

(65) Prior Publication Data
US 2016/0157753 A1 Jun. 9, 2016

Related U.S. Application Data

(60) Provisional application No. 62/089,474, filed on Dec. 9, 2014.

(51) Int. Cl.
| | |
|---|---|
| *A61B 5/04* | (2006.01) |
| *A61B 5/11* | (2006.01) |
| *A61B 5/0488* | (2006.01) |
| *A61B 5/0492* | (2006.01) |
| *A61B 5/00* | (2006.01) |

(52) U.S. Cl.
CPC .......... *A61B 5/1106* (2013.01); *A61B 5/0488* (2013.01); *A61B 5/0064* (2013.01); *A61B 5/0492* (2013.01); *A61B 5/7257* (2013.01); *A61B 2562/0219* (2013.01)

(58) Field of Classification Search
CPC ... A61B 5/1106; A61B 5/0488; A61B 5/0492; A61B 5/0064
USPC .................................................. 600/546, 547
See application file for complete search history.

(56) References Cited

U.S. PATENT DOCUMENTS

| | | | |
|---|---|---|---|
| 4,291,705 A * | 9/1981 | Severinghaus ...... | A61B 5/0488 600/546 |
| 6,002,960 A | 12/1999 | Sternberger et al. | |
| 2012/0071733 A1* | 3/2012 | Grey ................... | G06F 19/3481 600/546 |
| 2015/0230749 A1* | 8/2015 | Gharib ................ | A61B 5/0488 600/546 |
| 2016/0100808 A1* | 4/2016 | Anbarani ............ | A61B 5/0488 600/324 |

OTHER PUBLICATIONS

Sternberger, Wayne I. et al., "Neural Blockade Anesthesia Monitor," Johns Hopkins APL Technical Digest, vol. 25, No. 3 (Jul. 2004), pp. 231-241.

* cited by examiner

*Primary Examiner* — Max Hindenburg
*Assistant Examiner* — Jonathan M Foreman
(74) *Attorney, Agent, or Firm* — Sung T. Kim (57) ABSTRACT

An apparatus for neural block determination is provided including processing circuitry configured to receive muscle movement measurements, analyze the muscle movement measurements in a frequency domain, and determine an effectiveness of an anesthetic based on the analysis of the muscle movement measurements in the frequency domain.

20 Claims, 7 Drawing Sheets

NEURAL BLOCK DETERMINATION

CROSS REFERENCE TO RELATED APPLICATIONS

This application claims the benefit of U.S. Provisional Application No. 62/089,474 filed on Dec. 9, 2014, the entire contents of which are hereby incorporated herein by reference.

TECHNICAL FIELD

Example embodiments generally relate to pain management and, in particular, relate to neural block determination.

BACKGROUND

Typically clinicians, such as anesthetists, anesthesiologists, doctors, nurses, or the like, rely on subjective feedback from a patient to determine the effectiveness of a neural block or local anesthetic. Some example subjective feedback techniques include hot and cold sensation tests, and needle prick tests, performed after the anesthetic is administered. The subjectivity of these tests requires the cooperation of the patient, limiting them generally to humans or best guesses with non-human or uncooperative patients, e.g., sleeping adults, uncooperative adults (psychological or defiant), pediatric patients, or the like.

BRIEF SUMMARY OF SOME EXAMPLES

Accordingly, some example embodiments may enable an apparatus for neural block determination including processing circuitry configured to receive muscle movement measurements, analyze the muscle movement measurements in a frequency domain, and determine an effectiveness of an anesthetic based on the analysis of the muscle movement measurements in the frequency domain.

In another embodiment, a method for neural block determination is provided including receiving muscle movement measurements, analyzing the muscle movement measurements in a frequency domain, and determining an effectiveness of an anesthetic based on the analysis of the muscle movement measurements in the frequency domain.

BRIEF DESCRIPTION OF THE SEVERAL VIEWS OF THE DRAWING(S)

Having thus described the apparatus for neural block determination in general terms, reference will now be made to the accompanying drawings, which are not necessarily drawn to scale, and wherein:

DETAILED DESCRIPTION

Some example embodiments now will be described more fully hereinafter with reference to the accompanying drawings, in which some, but not all example embodiments are shown. Indeed, the examples described and pictured herein should not be construed as being limiting as to the scope, applicability or configuration of the present disclosure. Rather, these example embodiments are provided so that this disclosure will satisfy applicable legal requirements. Like reference numerals refer to like elements throughout. As used herein, operable coupling should be understood to relate to direct or indirect connection that, in either case, enables functional interconnection of components that are operably coupled to each other.

As used in herein, the terms "component," "module," and the like are intended to include a computer-related entity, such as but not limited to hardware, software, or a combination of hardware and software. For example, a component or module may be, but is not limited to being, a process running on a processor, a processor, an object, an executable, a thread of execution, and/or a computer. By way of example, both an application running on a computing device and/or the computing device can be a component or module. One or more components or modules can reside within a process and/or thread of execution and a component/module may be localized on one computer and/or distributed between two or more computers. In addition, these components can execute from various computer readable media having various data structures stored thereon. The components may communicate by way of local and/or remote processes such as in accordance with a signal having one or more data packets, such as data from one component/module interacting with another component/module in a local system, distributed system, and/or across a network such as the Internet with other systems by way of the signal. Each respective component/module may perform one or more functions that will be described in greater detail herein. However, it should be appreciated that although this example is described in terms of separate modules corresponding to various functions performed, some examples may not necessarily utilize modular architectures for employment of the respective different functions. Thus, for example, code may be shared between different modules, or the processing circuitry itself may be configured to perform all of the functions described as being associated with the components/modules described herein. Furthermore, in the context of this disclosure, the term "module" should not be understood as a nonce word to identify any generic means for performing functionalities of the respective modules. Instead, the term "module" should be understood to be a modular component that is specifically configured in, or can be operably coupled to, the processing circuitry to modify the behavior and/or capability of the processing circuitry based on the hardware and/or software that is added to or otherwise operably coupled to the processing circuitry to configure the processing circuitry accordingly.

As used herein, the term "neural block" shall be interpreted constantly with a nerve block, nerve blockade, or neural blockade.

Bio-physiological signals may be used to determine the location and density of a neural block objectively and quantitatively without reliance on patient feedback. As such the bio-physiological signals may be used to determine the effectiveness of an anesthetic or neural block, in instances in which the patient is non-human and/or uncooperative. Some example bio-physiological signals, may include without limitation, heart rate, respiration rate, muscle movement, skin temperature, neurological activity, or the like. The bio-physiological signals may be measured by various systems, such as electromyography (EMG), acoustic myography (AMG), electrocardiogram (EKG), temperature detectors, or the like.

In an example embodiment, the muscle movement may be measured, such as by an EMG. The muscle movement measurements may be analyzed in a frequency domain and a determination of an effectiveness of an anesthetic may be determined based on the muscle movement measurements in the frequency domain.

In an example embodiment, the analysis of the muscle movement in the frequency domain may include plotting the average power in a frequency band of interest, e.g., spectral power, over time. Determining the average spectral power of the muscle movement measurements in a frequency band of interest over time may be illustrative of the effectiveness of the anesthetic as inversely proportional to the power of the muscle movement measurements in the frequency band of interest. In some example embodiments, the muscle movement measurements may be received from a plurality of points on a patient's body and a location and/or density of a neural block may be determined based on a comparison of the muscle movement measurements in the frequency domain.

Example Apparatus

Figure 1:
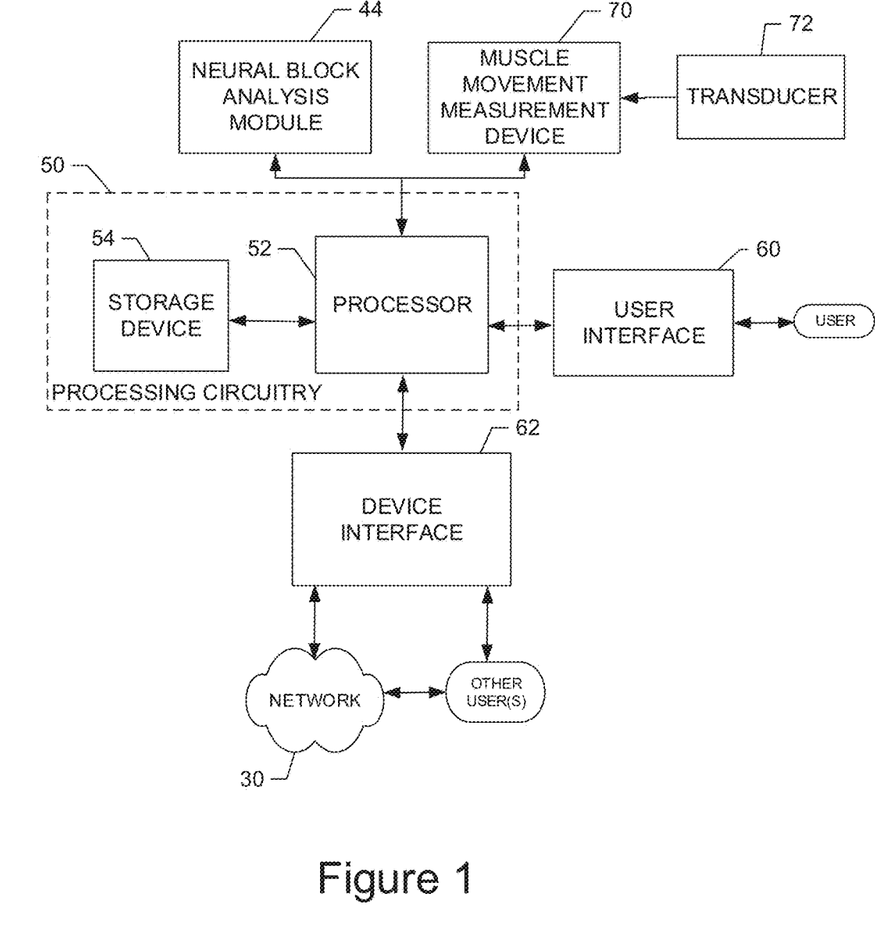
FIG. 1 illustrates an example apparatus for neural block determination according to an example embodiment.

An example embodiment of the invention will now be described with reference to FIG. 1. FIG. 1 shows certain elements of an apparatus for neural block determination according to an example embodiment. The apparatus of FIG. 1 may be employed, for example, on a client, a computer, a network access terminal, a personal digital assistant (PDA), cellular phone, smart phone, a network device, server, proxy, or the like. Alternatively, embodiments may be employed on a combination of devices. Accordingly, some embodiments of the present invention may be embodied wholly at a single device or by devices in a client/server relationship. Furthermore, it should be noted that the devices or elements described below may not be mandatory and thus some may be omitted in certain embodiments.

Referring now to FIG. 1, an apparatus configured to determine an effectiveness of a neural block is provided. In an example embodiment, the apparatus may include or otherwise be in communication with processing circuitry 50 that is configured to perform data processing, application execution and other processing and management services. In one embodiment, the processing circuitry 50 may include a storage device 54 and a processor 52 that may be in communication with or otherwise control, a neural block analysis module 44, a user interface 60, a device interface 62, and a muscle movement measurement device 70. As such, the processing circuitry 50 may be embodied as a circuit chip (e.g., an integrated circuit chip) configured (e.g., with hardware, software or a combination of hardware and software) to perform operations described herein. However, in some embodiments, the processing circuitry 50 may be embodied as a portion of a server, computer, laptop, workstation or even one of various mobile computing devices. In situations where the processing circuitry 50 is embodied as a server or at a remotely located computing device, the user interface 60 may be disposed at another device (e.g., at a computer terminal or client device) that may be in communication with the processing circuitry 50 via the device interface 62 and/or a network).

The user interface 60 may be in communication with the processing circuitry 50 to receive an indication of a user input at the user interface 60 and/or to provide an audible, visual, mechanical or other output to the user. As such, the user interface 60 may include, for example, a keyboard, a mouse, a joystick, a display, a touch screen, a microphone, a speaker, a cell phone, or other input/output mechanisms. In embodiments where the apparatus is embodied at a server or other network entity, the user interface 60 may be limited or even eliminated in some cases. Alternatively, as indicated above, the user interface 60 may be remotely located.

The device interface 62 may include one or more interface mechanisms for enabling communication with other devices and/or networks (e.g., network 30). In some cases, the device interface 62 may be any means such as a device or circuitry embodied in either hardware, software, or a combination of hardware and software that is configured to receive and/or transmit data from/to the network 30 and/or any other device or module in communication with the processing circuitry 50. In this regard, the device interface 62 may include, for example, an antenna (or multiple antennas) and supporting hardware and/or software for enabling communications with a wireless communication network and/or a communication modem or other hardware/software for supporting communication via cable, digital subscriber line (DSL), universal serial bus (USB), Ethernet or other methods. In situations where the device interface 62 communicates with a network, the network may be any of various examples of wireless or wired communication networks such as, for example, data networks like a Local Area Network (LAN), a Metropolitan Area Network (MAN), and/or a Wide Area Network (WAN), such as the Internet.

In an example embodiment, the storage device 54 may include one or more non-transitory storage or memory devices such as, for example, volatile and/or non-volatile memory that may be either fixed or removable. The storage device 54 may be configured to store information, data, applications, instructions or the like for enabling the apparatus to carry out various functions in accordance with example embodiments of the present invention. For example, the storage device 54 could be configured to buffer input data for processing by the processor 52. Additionally or alternatively, the storage device 54 could be configured to store instructions for execution by the processor 52. As yet another alternative, the storage device 54 may include one of a plurality of databases that may store a variety of files, contents or data sets, such as muscle movement measurements. Among the contents of the storage device 54, applications may be stored for execution by the processor 52 in order to carry out the functionality associated with each respective application.

The processor 52 may be embodied in a number of different ways. For example, the processor 52 may be embodied as various processing means such as a microprocessor or other processing element, a coprocessor, a controller or various other computing or processing devices including integrated circuits such as, for example, an ASIC (application specific integrated circuit), an FPGA (field programmable gate array), a hardware accelerator, or the like. In an example embodiment, the processor 52 may be configured to execute instructions stored in the storage device 54 or otherwise accessible to the processor 52. As such, whether configured by hardware or software methods, or by a combination thereof, the processor 52 may represent an entity (e.g., physically embodied in circuitry) capable of performing operations according to embodiments of the present invention while configured accordingly. Thus, for example, when the processor 52 is embodied as an ASIC, FPGA or the like, the processor 52 may be specifically configured hardware for conducting the operations described herein. Alternatively, as another example, when the processor 52 is embodied as an executor of software instructions, the instructions may specifically configure the processor 52 to perform the operations described herein.

In an example embodiment, the processor 52 (or the processing circuitry 50) may be embodied as, include or otherwise control the neural block analysis module 44, which may be any means, such as, a device or circuitry operating in accordance with software or otherwise embodied in hardware or a combination of hardware and software (e.g., processor 52 operating under software control, the processor 52 embodied as an ASIC or FPGA specifically configured to perform the operations described herein, or a combination thereof) thereby configuring the device or circuitry to perform the corresponding functions of the neural block analysis module 44 as described below.

The neural block analysis module 44 may include tools to facilitate neural block analysis. In an example embodiment, the neural block analysis module 44 may be configured to receive muscle movement measurements, analyze the muscle movement measurements in a frequency domain, and determine an effectiveness of an anesthetic based on the analysis of the muscle movement measurements in the frequency domain. The determination of effectiveness of the muscle movement measurements may be in real time or based on muscle movement measurements, stored in a memory, such as storage device 54.

The processing circuitry 50 may be in communication with the muscle movement measurement device 70. The muscle movement measurement device 70 may include an electromyogram (EMG), accelerometer, a strain gauge, a laser vibrometer, a microphone (e.g., spontaneous acoustomyogram), or the like. Although the examples herein are directed toward an embodiment in which the muscle movement measurement device is an EMG, one of ordinary skill in the art would immediately appreciate that similar methods may be used for other muscle measurement devices, such as the examples listed above.

In an example embodiment in which the muscle movement device 70 is an EMG, the EMG may be in communication with a transducer 72, such as an electrode. The transducer 72 may be a unipolar electrode or be a plurality of electrodes. In an example embodiment, the transducer 72 may be a needle electrode or an adhesive electrode. Utilization of multiple electrodes and/or needle electrodes may provide superior signal strength and clarity.

Example Neural Block Determination

Figure 2A:
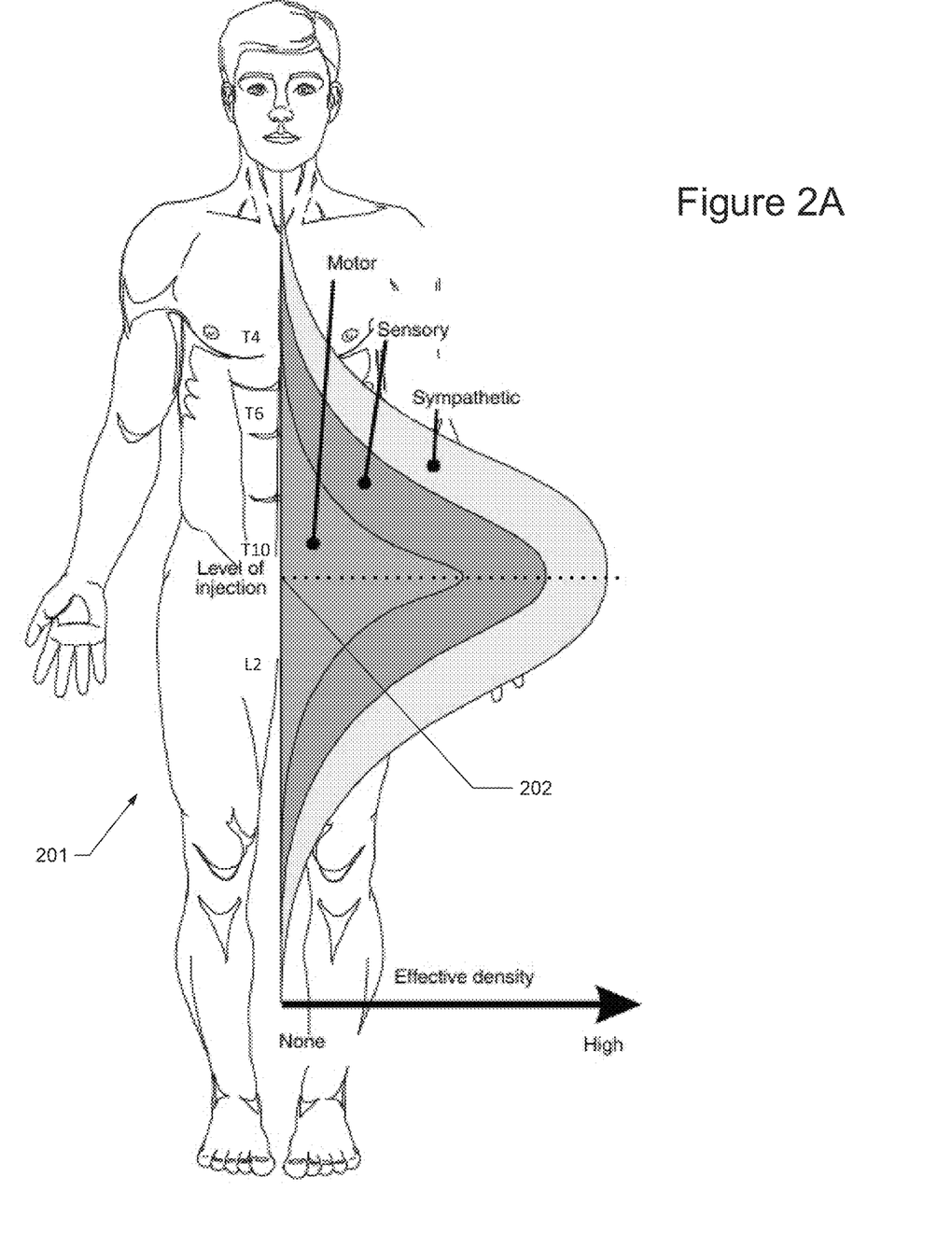
FIG. 2A illustrates an example neural block density graph of a patient according to an example embodiment.

FIG. 2A illustrates an example neural block density graph according to an example embodiment. A patient 201 may be injected with an anesthetic at an injection site 202. As the anesthetic takes effect the effective density of the anesthetic may be measured at points extending from the injection site 202. The anesthetic may affect (e.g., block) motor, sensory, parasympathetic, and/or sympathetic nerves. The sympathetic nerves may be blocked the farthest from the injection site 202, sensory nerves may be blocked closer to the injection site, and motor nerves may be blocked nearest to the injection site 202. The effects of the neural block may relate to the characteristics of the nerves affected and the anesthetic used to create the neural block. In an example embodiment, the measurement points may be dermatomes, such as dermatome L2, T4, T6, and T10. The effectiveness, e.g., local density, of the neural block may be expected to be greatest at the injection site 202 and diminish as the distance from the injection site 202 increases. In some embodiments, the effectiveness of the neural block may be described as block density or how "profound" the neural block is. Muscle movement may be measured at the measurement points. In some example embodiments, the muscle movement measurements may be accomplished using an EMG.

Figure 2B:
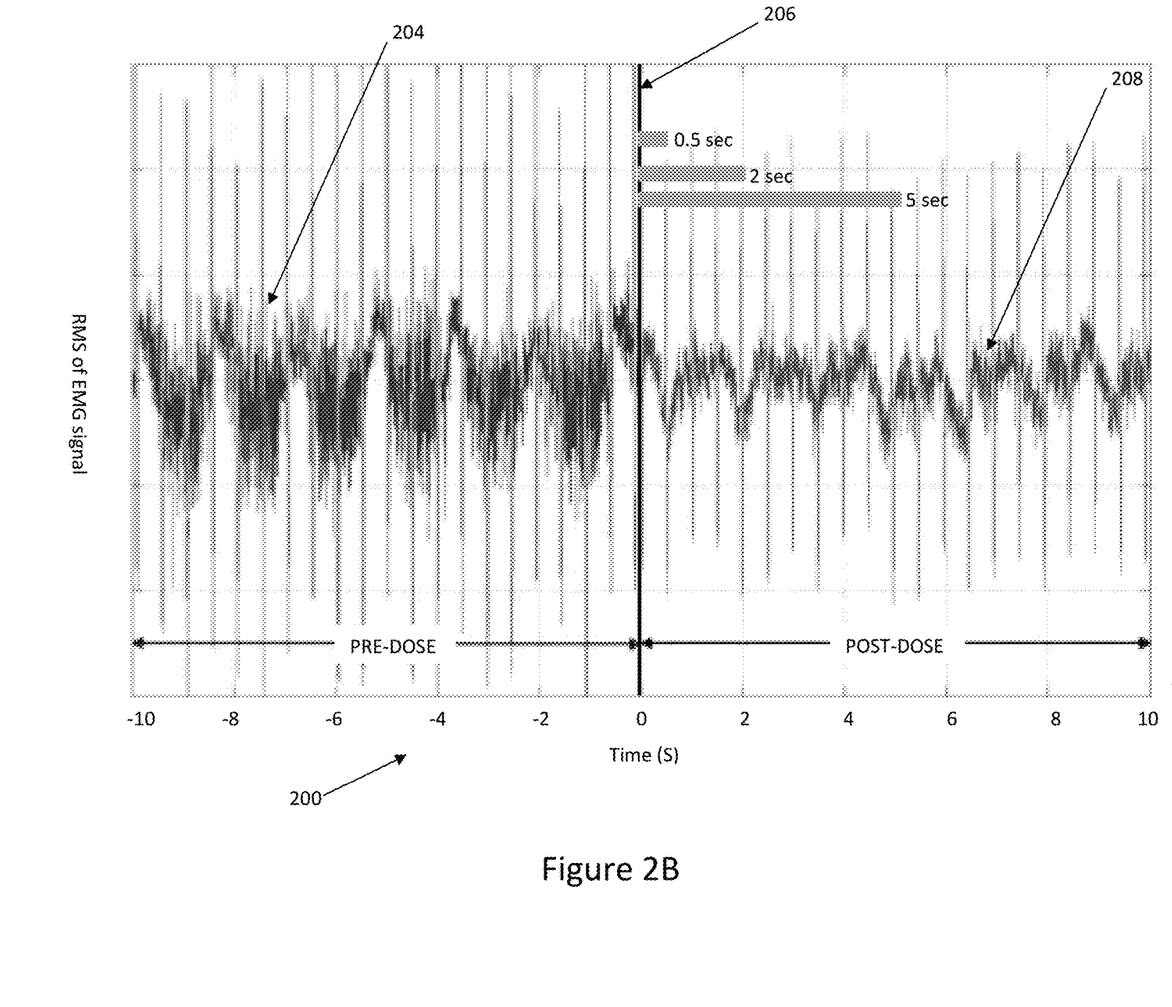
FIG. 2B illustrates an example electromyograph according to an example embodiment.

FIG. 2B illustrates an example electromyograph according to an example embodiment. An EMG may be connected to one or more measurement points, such as L2, T4, T6, and T10, on the patient 201. The EMG may output an electromyograph 200. In an example embodiment the muscle movement measurements may be analyzed in the time domain using the EMG signal level as a function of time. The EMG signal may be used to distinguish the muscle movement measurements "at rest" and "active". In some example embodiments, a root mean squared (rms) estimate may be applied to the EMG signal. The rms estimate may provide an average power indication over a finite integration interval, as follows:

$$\mathrm{rms} = \sqrt{\sum_{i=1}^{n} x_i^2 / n}$$

where $x_i$ are the time-sampled data and n is the number of samples in the integration interval. In some example embodiments, the rms estimate may be effective in distinguishing between at-rest and blocked EMG signal characteristics. In an example embodiment, the rms estimate may be effective in distinguishing between a regional block, such as a caudal block and a local block, such as a penile block.

As depicted in FIG. 2B, the rms estimate of the pre-anesthetic EMG signal 204, e.g., at rest, includes a significantly greater magnitude of signal amplitude than the post-anesthetic EMG signal 208. The anesthetic in the depicted example was administered at the time bar 206. In an example embodiment, the pre-anesthetic EMG signal 204, e.g., baseline, may be compared to the post-anesthetic EMG signal 208 to determine a change in EMG signal. The change in EMG signal may be compared to a change threshold, such as predetermined value or percentage. A change in EMG signal which satisfies the change threshold may be determined to be an effective neural block. In some embodiments, the change in EMG signal may be compared to more than one change threshold or change threshold ranges to determine an effectiveness of the neural block.

As an estimate of power of the EMG, the rms estimate may include the full band width of the EMG signal, which may include significant narrow-band noise artifacts and wide-band transients.

Figure 3:
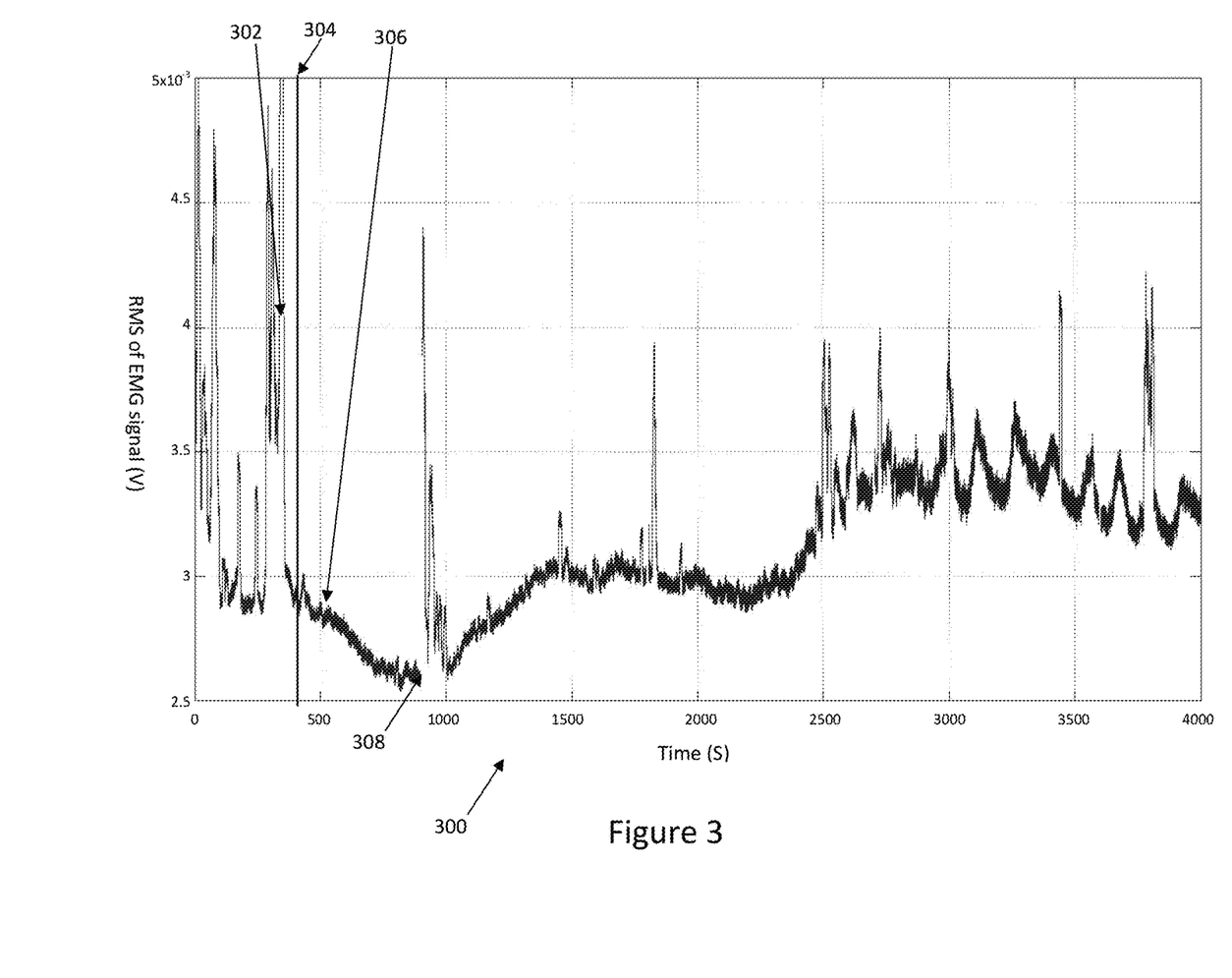
FIG. 3 illustrates an example rms plot of an electromyogram according to an example embodiment.
Figure 4:
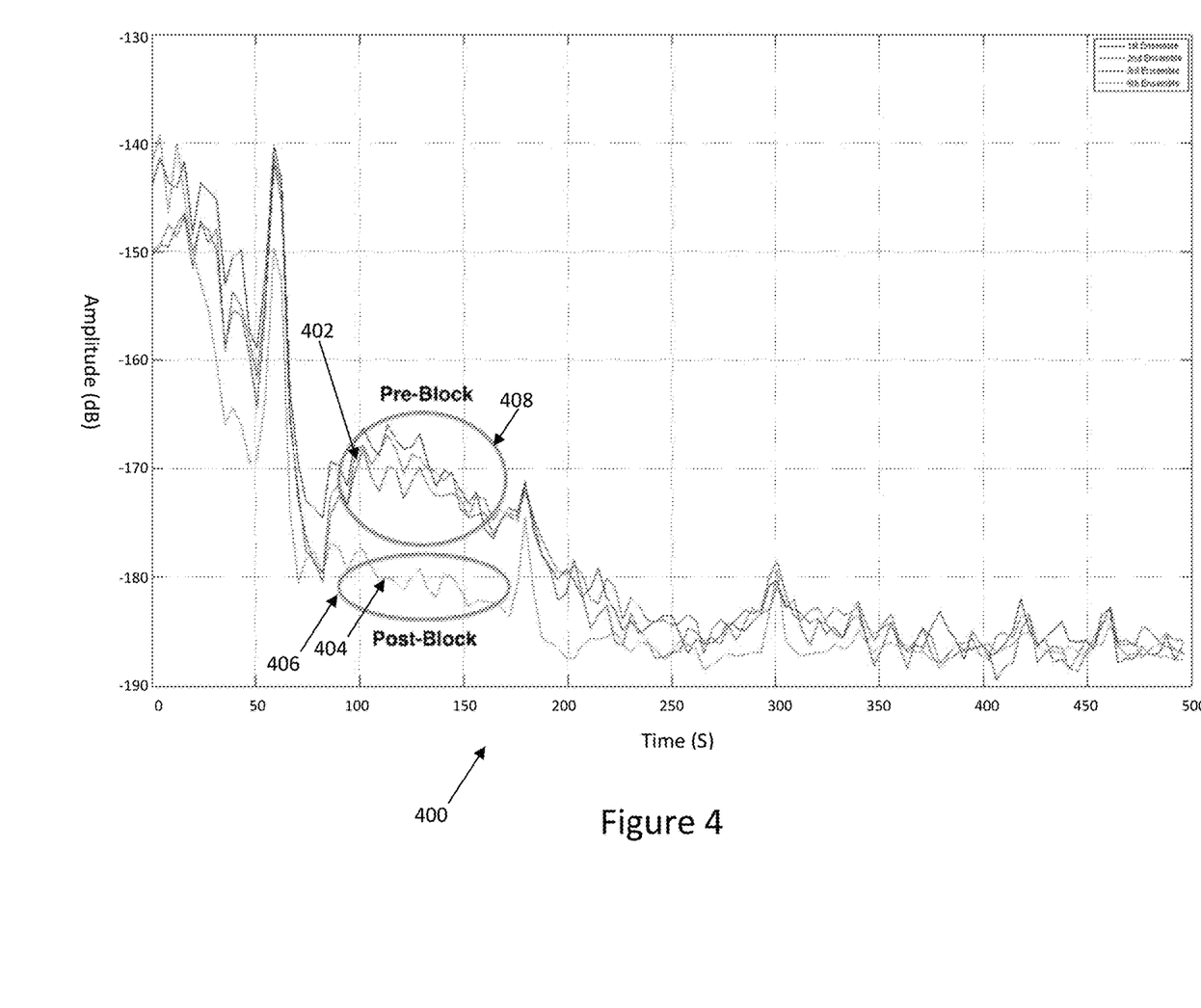
FIG. 4 illustrates an example electromyogram in the frequency domain according to an example embodiment.
Figure 5:
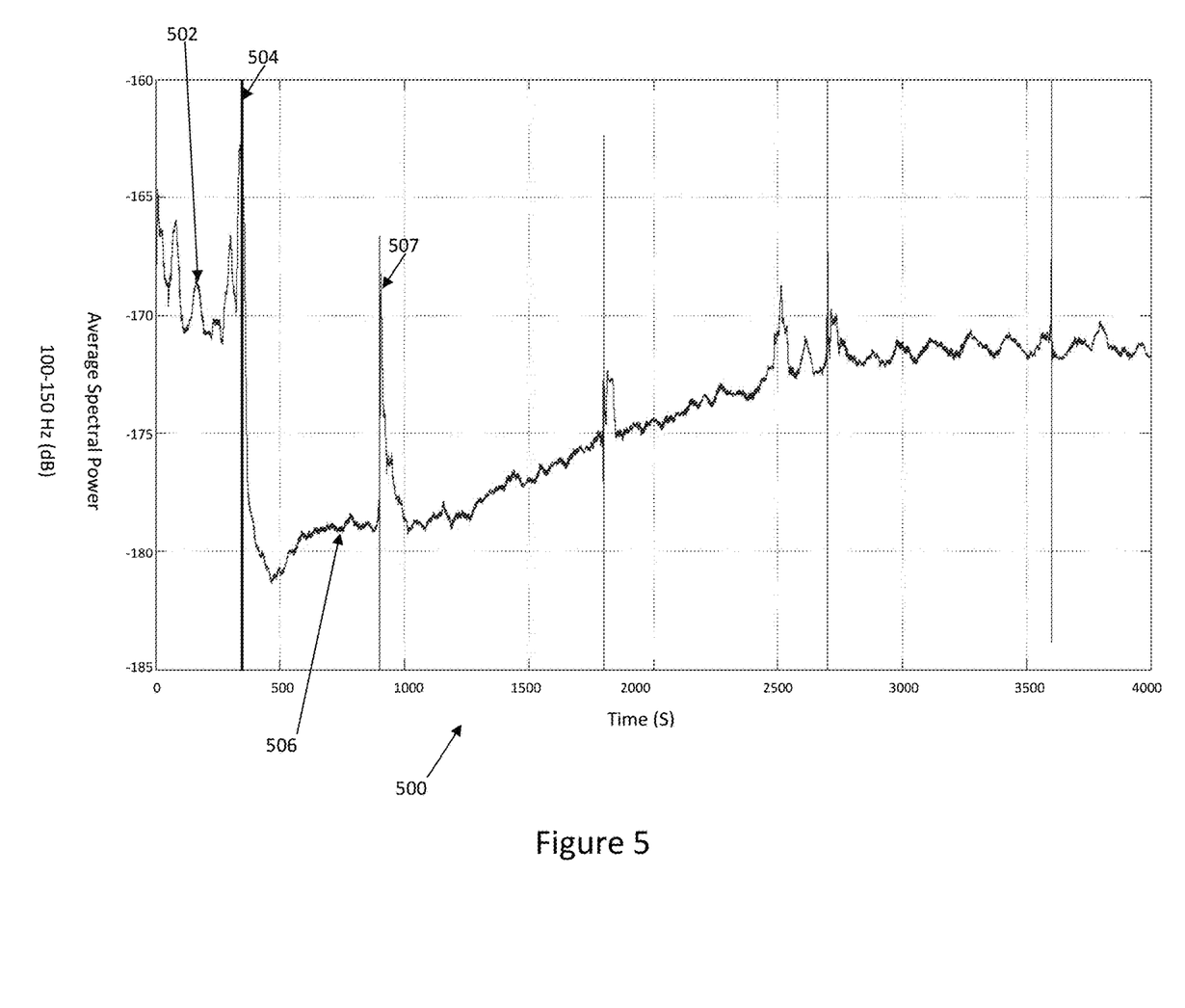
FIG. 5 illustrates an example average pass-band spectral power plot over time of electromyogram according to an example embodiment.

FIGS. 3-5 illustrate an example analysis of an EMG signal received from a pig to determine the effectiveness of an epidural anesthetic.

FIG. 3 illustrates an example rms estimate plot 300 of an electromyogram according to an example embodiment. The rms estimate plot 300 is of the T10 (lower thoracic) EMG signal using a 10-second integration interval. Successive rms estimate plot values may be computed by dropping the first data value and adding one data value to the end of the sequence in a sliding window manner. A pre-anesthetic EMG signal 302 may be determined as a baseline. In the present example, the anesthetic was administered at a time of 300 seconds, as depicted by time bar 304. The post-anesthetic EMG signal 306 may be monitored to determine the effectiveness and/or changes of the neural block, as described above.

In the present example, after the anesthetic was administered at bar time 304, no other interventions were applied. The post-anesthetic EMG signal 306 initially drops as expected immediately after administration of the anesthetic. The EMG signal 306 may be expected to return to a value, as a function of time, that is similar to the pre-anesthetic value as a reflection of the offset of the anesthetic.

FIG. 4 illustrates an example electromyogram in the frequency domain 400 according to an example embodiment. In an example embodiment, the EMG signal may be analyzed in the frequency domain. In some example embodiments, a frequency domain method may be applied to the EMG signal, such as power spectral density by fast Fourier transform, ensemble averaging, or the like. Finite frequency bands, e.g., frequency bands of interest, may exhibit notable differences in power levels as a function of whether the muscle associated with the muscle movement measurement was affected by a neural block or not affected by a neural block.

The electromyogram in the frequency domain 400 includes frequency on the x axis of 0-500 Hz and amplitude on the y axis as a function of frequency (dB). The EMG signal in the frequency domain samples may be collected with a sampling rate of 1000/second and 16 bits of resolution. In an example embodiment, the difference between the spectra of a T10 EMG signal measured before and after administering the epidural block is depicted. The pre-block EMG signals in the frequency domain 402 may be compared to the post block EMG signals in the frequency domain 404. A post block indication 406 is depicted by about a 10 dB decrease in the power level over the frequency band of approximately 100-150 Hz, compared to the pre-block EMG signal in the same frequency band 408. Lesser decreases may be observed both above and below this band. The clear difference in power in the 100-150 Hz frequency band may not be observed in other portions of the power spectrum. Equally important is the observation that the post-block power level returns to pre-block power level values as the anesthetic block wears off over time, as depicted in FIG. 5, which may be consistent with the expected pharmacodynamics of the anesthetic.

In an example embodiment, a band pass filter may be applied to the EMG signal to isolate the frequency of interest, such as 100-150 Hz, in the present example. Additionally, the EMG signal over time, such as depicted in FIG. 2B, may be frequency transformed. In an example embodiment the EMG signal over time may be frequency transformed by applying a 256 value fast Fourier transform with successive transform windows that slide by 16 samples. The mean power in each frequency bin may be calculated as a function of time that corresponds to the EMG signal over time. The mean of the power in the frequency bins may correspond to the frequency band of interest, such as 100-150 Hz in the present example. The output of the frequency transform may be the average spectral power (ASP) plotted over time 500 as depicted in FIG. 5.

FIG. 5 illustrates an example spectral power plot over time of an electromyogram according to an example embodiment. The average spectral power plotted over time 500 may include pre-anesthetic ASP 502 and post-anesthetic ASP 506. The administration of the anesthetic is depicted by time bar 304. In some example embodiments, the frequency transform processing of the EMG signal may be divided into time segments, such as 900 seconds. The division of the frequency transform processing may account for computational processing demands. The segments may be stitched together after the frequency transform processing. In some example embodiments, the stitching may result in stitching artifacts 507 at the segment boundaries. The stitching artifacts 507 may not be indicative of the underlying data, and in some embodiments, may be filtered, such as by application of a pop filter. In some example embodiments, the EMG signal may be analyzed in as a continuous data stream to prevent stitching artifacts 507.

In the example depicted, in FIG. 5, the x axis is the average spectral power in the 100-150 Hz band in a range of −160 to −185 dB, and the y axis is time 0-4000 seconds. As discussed above, the anesthetic is administered at 300 seconds, as depicted by time bar 304. The pre-anesthetic ASP 502 fluctuates between about −165 and −170 dB. After the administration of the anesthetic at the time bar 304, the post-anesthetic ASP 506 decreases immediately to about −181 dB at about 450 seconds; increases as a function of time, to about −173 dB at about 2700 seconds; and fluctuates between −173 and −171 dB from 2700 to 4000 seconds.

The effectiveness of a neural block may be determined based on the analysis of the muscle movement in the frequency domain. In an example embodiment, the ASP plot 500 may be displayed, such as on user interface 60. Additional or alternatively, an ASP value based on the ASP plot may be displayed. In some example embodiments, historical ASP data based on the patient, like patients, the anesthetic or the like may be used to determine an ASP value indicative of an effective neural block. A clinician, such as a doctor, an anesthetist, a nurse, or the like, may use the ASP plot 500 or ASP value indicative of an effective neural block to manually determine the effectiveness the anesthetic based on changes in the ASP over time or based on a predetermined ASP value.

In another example embodiment, the effectiveness of the anesthetic may be determined automatically, such as by the processing circuitry 50. In an example embodiment, the pre-anesthetic ASP 502 may be compared to the post-anesthetic ASP 506 to determine an ASP change. The ASP change may be compared to a predetermined ASP change threshold, such as a pre-determined change value or percentage of the pre-anesthetic ASP 502. In an example embodiment, the ASP change threshold may be 10 dB, an ASP change which satisfies the ASP change threshold may be determined to be an effective neural block, and an ASP change which fails to satisfy the ASP change threshold may be determined to be a failed neural block.

In an example embodiment, the pre-anesthetic ASP 502 and post-anesthetic ASP 506 may be compared in real time. In one such example embodiment, a control area may be designated on a patient, which will not undergo anesthesia. Muscle movement measurements of the control area, such as a leg not undergoing a medical procedure, may be utilized to determine a pre-anesthetic ASP 502. The post anesthetic ASP 506 may be determined from the muscle movement measurements of the area in which the anesthetic is applied, such as a second leg undergoing the medical procedure.

In some example embodiments, a second ASP change threshold may be set based on an effective neural block. The second ASP change threshold may be used to determine when anesthetic is wearing off prior to the neural block not being effective. In an example embodiment, the second ASP change threshold may be set at 5 dB above the lowest ASP value after satisfying the ASP change threshold, which may be the initial decrease in ASP after administering the anesthetic. In some embodiments, one or more additional ASP change thresholds may be used to determine the effectiveness of the neural block. Although, discussed in the context of automatic determinations, a technician may use the ASP change thresholds or similar thresholds in the manual determination of the effectiveness of the anesthetic.

Using the present example, a pre-anesthetic ASP 502 may be −168 dB. The first ASP threshold, e.g., 10 dB decrease, may be set as −178 dB, which would be satisfied at about 350 seconds, and the neural block determined to be effective. The second ASP change threshold may be set at the lowest ASP value reached after the neural block is determine to be effective, e.g., about −181 dB at about 450 second. The second ASP change threshold would determine the neural block to be ineffective or approaching ineffective at −173 dB, e.g., 5 dB above the lowest ASP value, at about 1600 seconds.

In some example embodiments, the muscle movement measurements may be taken at a plurality of point on the patient 201, such as L2, T4, T6, and T10. In an example embodiment, the analysis of the muscle movement measurements in the frequency domain, as discussed above may be performed on muscle movement measurements at each of the respective points on the patient 201. The muscle movement measurements may be compared in the frequency domain to determine the level and density of the neural block. As discussed above the, local effectiveness, e.g. density, of the neural block may be higher closer to the anesthetic injection point 202, and/or the location at which the anesthetic is effective. The comparison of the muscle movement measurements in the frequency domain may be used to determine the location of the neural block by plotting the density of the neural block at the respective points on the patient 201.

Additionally or alternatively, an ASP associated with a muscle movement measurement may be compared to the ASP value indicative of an effective neural block to determine an ASP value difference. The ASP value difference may be compared to the ASP difference threshold, in a manner substantially similar to the ASP change threshold discussed above.

In an example embodiment, the location and density of the neural block based on the ASP change thresholds or ASP value difference threshold may be displayed on the user interface 60 as color or shade code or a body outline or portion thereof. In an example embodiment, an effective block may be indicated as green and an ineffective or failed block indicated as red. In some example embodiments, other shades may be used to indicate effective or densities associated with the particular location and the dynamic changes that occur over time.

Example Neural Block Determination Flow Chart

Figure 6:
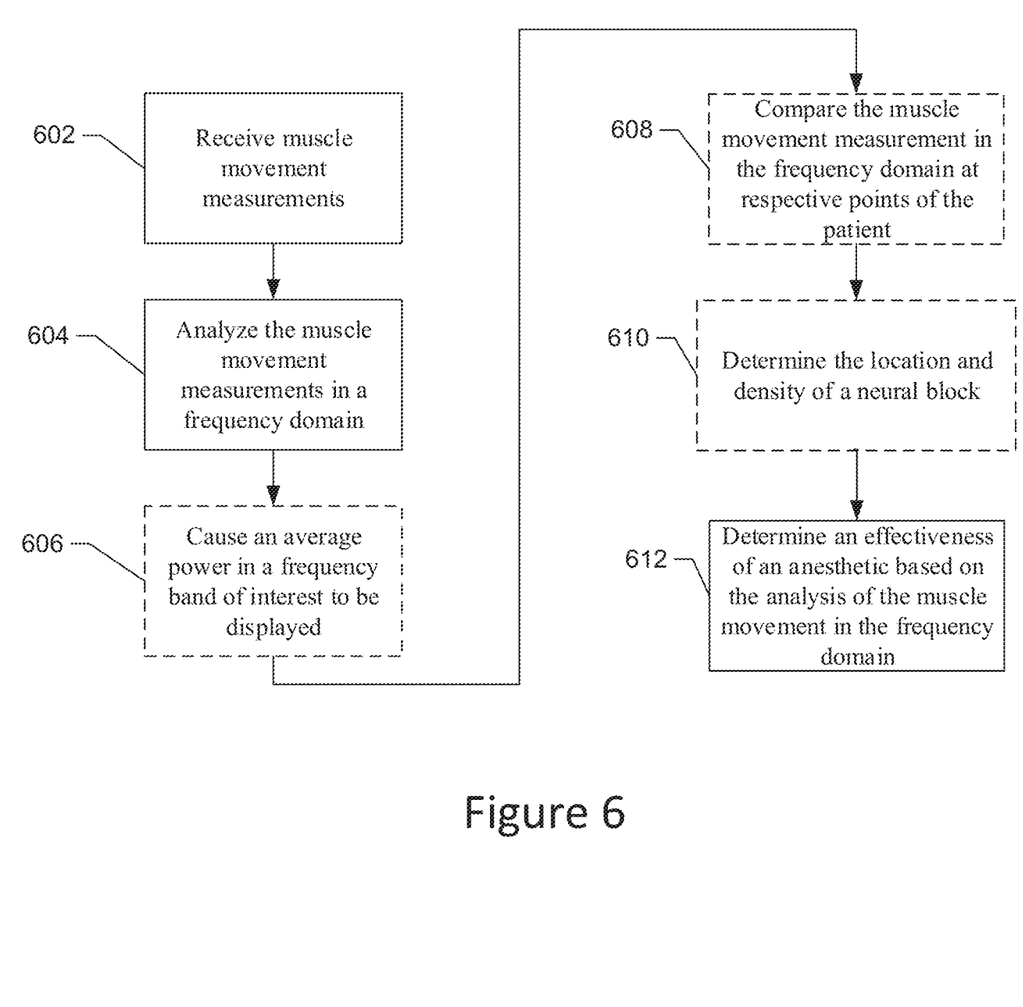
FIG. 6 illustrates a method for neural block determination according to an example embodiment.

From a technical perspective, the neural block analysis module 44 described above may be used to support some or all of the operations described above. The apparatus described in FIG. 1 may be used to facilitate the implementation of several computer program and/or network communication based interactions. As an example, FIG. 6 is a flowchart of a method and program product according to an example embodiment of the invention. It will be understood that each block of the flowchart, and combinations of blocks in the flowchart, may be implemented by various means, such as hardware, firmware, processor, circuitry and/or other device associated with execution of software including one or more computer program instructions. For example, one or more of the procedures described above may be embodied by computer program instructions. In this regard, the computer program instructions which embody the procedures described above may be stored by a memory device of a user terminal and executed by a processor in the user terminal. As will be appreciated, any such computer program instructions may be loaded onto a computer or other programmable apparatus (e.g., hardware) to produce a machine, such that the instructions which execute on the computer or other programmable apparatus create means for implementing the functions specified in the flowchart block(s). These computer program instructions may also be stored in a computer-readable memory that may direct a computer or other programmable apparatus to function in a particular manner, such that the instructions stored in the computer-readable memory produce an article of manufacture which implements the functions specified in the flowchart block(s). The computer program instructions may also be loaded onto a computer or other programmable apparatus to cause a series of operations to be performed on the computer or other programmable apparatus to produce a computer-implemented process such that the instructions which execute on the computer or other programmable apparatus implement the functions specified in the flowchart block(s).

Accordingly, blocks of the flowchart support combinations of means for performing the specified functions and combinations of operations for performing the specified functions. It will also be understood that one or more blocks of the flowchart, and combinations of blocks in the flowchart, can be implemented by special purpose hardware-based computer systems which perform the specified functions, or combinations of special purpose hardware and computer instructions.

In this regard, a method according to one embodiment of the invention is shown in FIG. 6. The method may be employed for neural block determination. The method may include, receiving muscle movement measurements, at operation 602. The method may also include analyzing the muscle movement measurements in a frequency domain, at operation 604. At operation 612, the method may include determining an effectiveness of an anesthetic based on the analysis of the muscle movement in the frequency domain.

In an example embodiment, the method may optionally include, as denoted by the dashed box, causing an average power in a frequency band of interest to be displayed, at operation 606. The method may optionally include comparing the muscle movement measurement in the frequency domain at respective points of the patient, at operation 608, and determining the location and density of a neural block, at operation 610.

In an example embodiment, an apparatus for performing the method of FIG. 6 above may comprise a processor (e.g., the processor 52) or processing circuitry configured to perform some or each of the operations (602-612) described above. The processor may, for example, be configured to perform the operations (602-612) by performing hardware implemented logical functions, executing stored instructions, or executing algorithms for performing each of the operations. In some example embodiments, the processor or processing circuitry may be further configured for additional operations or optional modifications to operations 602-612. In this regard, for example in an example embodiment, the analysis of the muscle movement measurements in the frequency domain also includes causing an average power in a frequency band of interest to be displayed. In some example embodiments, the muscle movement measurements are taken at a plurality of points on a patient and determining the effectiveness of an anesthetic also includes determining the location and density of a neural block based on a comparison of the muscle movement measurement in the frequency domain at respective points of the patient. In an example embodiment, the muscle movement measurements are received from an electromyogram. In some example embodiments, the electromyogram includes adhesive measurement electrodes or needle measurement electrodes. In an example embodiment, the electromyogram comprises at least two electrodes. In some example embodiments, the electromyogram comprises a unipolar electrode. In an example embodiment, the muscle movement measurements are received from an accelerometer, a laser vibrometer, or microphone. In some example embodiments, the processing circuitry is further configured to apply a band pass filter to the muscle movement measurements. In an example embodiment, the band pass filter is configured to pass frequencies of about 100-150 Hz.

Many modifications and other embodiments of the measuring device set forth herein will come to mind to one skilled in the art to which these inventions pertain having the benefit of the teachings presented in the foregoing descriptions and the associated drawings. Therefore, it is to be understood that the measuring devices are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In cases where advantages, benefits or solutions to problems are described herein, it should be appreciated that such advantages, benefits and/or solutions may be applicable to some example embodiments, but not necessarily all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

That which is claimed:

1. A system for neural block determination, the system comprising:
a muscle movement measurement device configured to measure muscle movement measurements at a plurality of points on a body extending away from an anesthetic injection site, each point in the plurality of points on the body being associated with a dermatome, and to transmit at least one digital signal representative of the muscle movement measurements at the plurality of points on the body; and
a neural block analysis module comprising processing circuitry configured to receive the at least one digital signal representative of the muscle movement measurements, analyze the muscle movement measurements in a frequency domain, and determine a location and a density corresponding to a neural block applied to the body based on a comparison of the muscle movement measurements measured at the plurality of points on the body;
wherein the processing circuitry is further configured to display, on a display device of a user interface, the location of the neural block on the body by plotting the density of the neural block at the plurality of points on the body to provide an indication of a current effectiveness of the neural block.

2. The system of claim 1, wherein the muscle movement measurements include pre-anesthetic and post-anesthetic muscle movement measurements, and
wherein the neural block analysis module is further configured to compare the pre-anesthetic muscle movement measurements to the post-anesthetic muscle movement measurements.

3. The system of claim 1, wherein the neural block analysis module is further configured to compare the muscle movement measurements to a first predetermined muscle movement value.

4. The system of claim 1, wherein the neural block analysis module is further configured to cause an average power associated with the muscle movement measurements in a frequency band of interest to be displayed on a user interface.

5. The system of claim 1, wherein the muscle movement measurement device comprises an electromyogram.

6. The system of claim 5, wherein the electromyogram comprises at least one of adhesive measurement electrodes or needle measurement electrodes.

7. The system of claim 5, wherein the electromyogram comprises at least two electrodes.

8. The system of claim 5, wherein the electromyogram comprises a unipolar electrode.

9. The system of claim 1, wherein the muscle movement measurement device comprises at least one of an accelerometer, a laser vibrometer, or a microphone.

10. The system of claim 1, wherein the processing circuitry is further configured to:
apply a band pass filter to the muscle movement measurements.

11. The system of claim 10, wherein the band pass filter is configured to pass frequencies in a predefined frequency band.

12. A method for neural block determination, the method comprising:
receiving, at a neural block analysis module, at least one digital signal representative of muscle movement measurements that are measured at a plurality of points on a body extending away from an anesthetic injection site;
analyzing, at the neural block analysis module, the muscle movement measurements in a frequency domain;
determining a location and a density corresponding to a neural block applied to the body based on a comparison of the muscle movement measurements measured at the plurality of points on the body; and
causing the location of the neural block on the body to be displayed on a display device by plotting the density of the neural block at the plurality of points on the body to provide an indication of a current effectiveness of the neural block.

13. The method of claim 12, wherein the muscle movement measurements include pre-anesthetic and post-anesthetic muscle movement measurements, and
wherein analyzing the muscle movement measurements in the frequency domain includes comparing the pre-anesthetic muscle movement measurements to the post-anesthetic muscle movement measurements.

14. The method of claim 12, wherein analyzing the muscle movement measurements includes comparing the muscle movement measurements to a first predetermined muscle movement value.

15. The method of claim 14, wherein analyzing the muscle movement measurements includes comparing the muscle movement measurements to a second predetermined muscle movement value indicating that the neural block is wearing off.

16. The method of claim 12, further comprising:
causing an average power associated with the muscle movement measurements in a frequency band of interest to be displayed on a user interface.

17. The method of claim 12, wherein the at least one digital signal representative of the muscle movement measurements are received from an electromyogram.

18. The method of claim 17, wherein the electromyogram comprises at least two electrodes.

19. The method of claim 12, wherein the at least one digital signal representative of the muscle movement measurements are received from at least one of an accelerometer, a laser vibrometer, or a microphone.

20. A system for determining effectiveness of a neural block applied on a body, the system comprising:
a neural block analysis module comprising processing circuitry configured to:
receive at least one digital signal representative of muscle movement measurements that are measured at a plurality of points on the body extending away from an anesthetic injection site,
analyze the muscle movement measurements in a frequency domain including comparing the muscle movement measurements measured at the plurality of points on the body,
determine a location and a density corresponding to the neural block based on the comparing, and
display, on a display device, the location of the neural block on the body by plotting the density of the neural block at the plurality of points on the body.

* * * * *